United States Patent [19]

Kondo et al.

[11] Patent Number: 4,653,504
[45] Date of Patent: Mar. 31, 1987

[54] ULTRASONIC PROBE

[75] Inventors: Toshio Kondo, Kunitachi; Yutaka Sato, Kashiwa, both of Japan

[73] Assignee: Hitachi Medical Corporation, Tokyo, Japan

[21] Appl. No.: 716,939

[22] Filed: Mar. 28, 1985

[30] Foreign Application Priority Data
May 28, 1984 [JP] Japan .................. 59-106386

[51] Int. Cl.⁴ ............................................. A61B 10/00
[52] U.S. Cl. ...................................... 128/660; 73/644
[58] Field of Search .................. 128/660, 661; 73/642, 73/644

[56] References Cited
U.S. PATENT DOCUMENTS 4,391,281  5/1983  Green .................................. 128/660
4,542,745  9/1985  Oakley ............................ 128/660 X
4,550,608  11/1985  Carnes et al. ........................ 128/660

Primary Examiner—Kyle L. Howell
Assistant Examiner—Francis J. Jaworski
Attorney, Agent, or Firm—Antonelli, Terry & Wands

[57] ABSTRACT

A probe for use in an ultrasonic diagnostic apparatus in which the acoustic impedance of a liquid medium put between the oscillator and the living body is made equal to that of the casing having the medium sealed therein, by using a low molecular weight polymer product of chlorotrifluoroethylene as the liquid medium. This can suppress the multi-reflection echoes within the casing to thereby improve the quality of the tomographic images obtained by the apparatus.

16 Claims, 9 Drawing Figures

ANGLE OF ROTATION $\phi$ OF MOTOR (deg.)

ULTRASONIC PROBE

BACKGROUND OF THE INVENTION

This invention concerns a probe for use in an ultrasonic diagnostic apparatus and, more specifically, it relates to an ultrasonic liquid medium for use in a probe adapted to use a liquid medium with a sonic velocity being lower than that in a living body between the oscillator and the living body for increasing the angle of deflection of the ultrasonic beam.

Fluorine-incorporated hydrocarbons, have been proposed as a liquid medium with a sonic velocity therein significantly lower than that in the living body and capable of attaining impedance matching easily with the living body (Japanese Patent Laid-open Publication (KOKAI) No. 85491/1978). However, the material of this kind is easily evaporable having a high vapor pressure of 1-230 torr (25° C.), for example, as seen in FC-72, FC-77, FC-104, FC-75, FC-40 and FC-43. In addition, their high gas-solubilizing effect leads to a defect of tending to form gas bubbles therein when applied to the ultrasonic probe. It is also apparent that commercially available fluorinated hydrocarbons are easily evaporable due to their low boiling points such as 57.7° C. for $C_6F_{14}$, 125.5° C. for $C_9F_{20}$, 47.6° C. for $C_2Cl_3F_3$ and 97.2° C. for $C_8F_{16}O$ at 1 atm.

SUMMARY OF THE INVENTION

This invention intends to make the acoustic impedance of a liquid medium, put between an oscillator and a living body, equal to the acoustic impedance of a casing in which the medium is sealed and the acoustic impedance of which is approximated to that at the surface of the living body. This minimizes the reflections at the interface in a probe for use in an ultrasonic diagnostic apparatus, whereby the multideflection echoes within the casing can be suppressed to thereby improve the quality of the tomographic images obtained by the diagnostic apparatus.

A probe for use with the ultrasonic diagnostic apparatus requires an acoustic medium with a sonic velocity lower than that in the living body and capable of easily attaining an acoustic impedance matching with the living body in order to deflect or converge the ultrasonic beam. This invention provides a liquid acoustic medium satisfying the above-mentioned requirements. As the acoustic medium in the probe it is important, in addition to acoustic properties, that the medium has satisfactory electrical properties such as insulation performance, as well as viscosity and lubricating property when applied to a mechanical scanning system. Further, the medium has to be non-toxic and less corrosive to metal and plastic materials. The present inventors have found low molecular weight polymer products of chlorotrifluoroethylene as a suitable material for the acoustic medium capable of satisfying these requirements and accomplished this invention.

BRIEF DESCRIPTION OF THE INVENTION

FIGS. 1 and 2 are graphs showing acoustic characteristics of low molecular weight polymer products from chlorotrifluoroethylene, FIGS. 3 through 5 are structural views for the mechanical scanning probe for use in the embodiment of this invention, FIG. 6 is a view for explanating the principle thereof, FIG. 7 is a chart of characteristics obtained where this invention is applied to the probe shown in FIGS. 3 through 5, FIG. 8 is a view for explanating the principle of the characteristics of the mechanical scanning probe applied with this invention, and FIG. 9 is a view for explanating the embodiment in which this invention is applied to an electronic curved linear probe.

DETAILED DESCRIPTION OF THE INVENTION

Explanation will now be made to the characteristic of low molecular weight polymer products from chlorotrifluoroethylene as the acoustic medium which is an essential factor in this invention. The low molecular weight polymer product from chlorotrifluoroethylene has a structure as shown below:

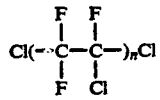

wherein fluorine atoms (F) and chlorine atoms (Cl) are bonded to the skeleton, both ends of which are completely stabilized with chlorine, and includes those of various molecular weight depending on the value of n (1, 2, 3, 4, 5 or 6). Sonic velocity and density were measured for the material comprising about 97% of low molecular weight polymer product from chlorotrifluoroethylene with n=2 in the molecular formula, the material comprising about 97% of low molecular weight chlorotrifluoroethylene with n=3 in the above molecular formula and a mixture comprising both of the above mentioned materials in an adequate ratio, to determine the relationship between the average molecular weight versus the sonic velocity and the acoustic impedance of the chlorotrifluoroethylene.

TABLE 1

| | Result of analysis for CTFE oil | | | | | |
|---|---|---|---|---|---|---|
| | Molecular formula | | | | | |
| | Cl(—CF₂—CFCl—)Cl | Cl(—CF₂—CFCl—)₂Cl | Cl(—CF₂—CFCl—)₃Cl | Cl(—CF₂—CFCl—)₄Cl | Cl(—CF₂—CFCl—)₅Cl | Cl(—CF₂—CFCl—)₆Cl |
| Product No. | Molecular weight | | | | | |
| | 187.36 | 303.85 | 420.32 | 536.79 | 635.26 | 769.73 |
| S-316 | 0.060 | 96.806 | 1.006 | 0.270 | 0.039 | 0.010 |
| S-519 | 0.062 | 2.556 | 95.895 | 0.085 | — | — |
| #1 | — | 0.523 | 39.996 | 45.241 | 11.139 | 2.099 |
| #3 | — | — | 3.706 | 42.143 | 49.183 | 3.926 |

Table 1 shows the component (% by weight) of CTFE oil (Trade name for the product manufactured by DAIKIN INDUSTRIES, LTD.) used to obtain the result of the experiment described hereinafter. These values were confirmed on the gas chromatographic analysis. In the analytical result shown in Table 1, although the total value for each of the components does not amount to 100% since they contain a little unknown impurity in addition to the low molecular weight polymer product from chlorotrifluoroethylene in which n=1-6, this difference may be considered negligibly small and gives no substantial effect on the conclusion in the following description.

TABLE 2

| Average molecular weight of CTFE oil | |
|---|---|
| Number of product | Average molecular weight |
| S-316 | 306.84 |
| S-519 | 415.94 |
| #1 | 492.68 |
| #3 | 590.04 |

Figure 1:
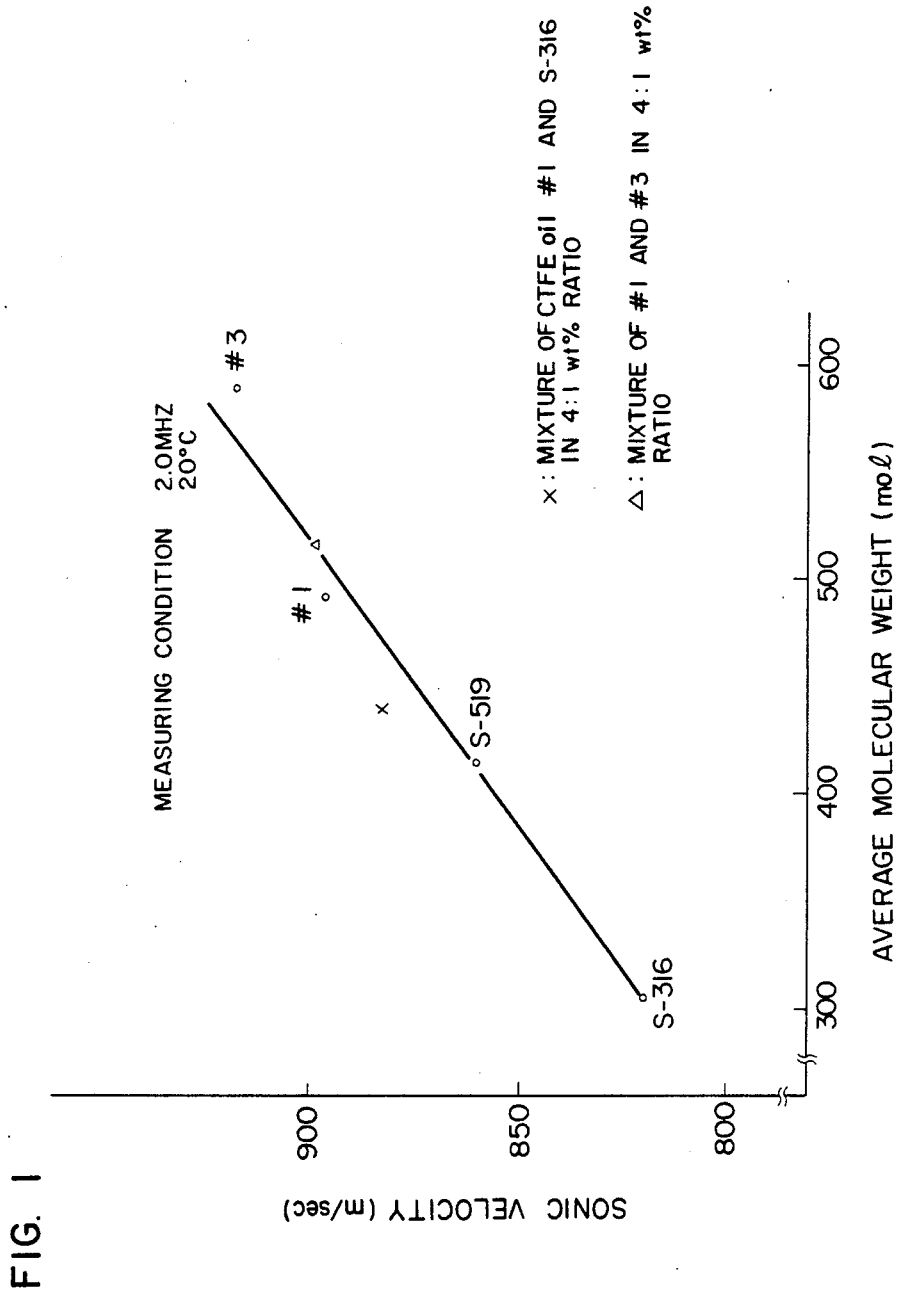

The average molecular weights for the low molecular weight polymer products from chlorotrifluoroethylene, that is, S-316, S-519, #1 and #3 shown in Table 1 are calculated as shown in Table 2. FIG. 1 shows an example of measurement for the relationship between the average molecular weight and the sonic velocity in the low molecular weight polymer products from chlorotrifluoroethylene and a mixture prepared by selecting and mixing two kinds of the products in an appropriate ratio shown in the table. It has already be known that the sonic velocity in such low molecular weight polymer products from chlorotrifluoroethylene is lower than that in a living body and also depends on the molecular weight, for example, as described in the report by R.T. Lagemann, et al. Ultrasonic Velocity in Some Liquid Fluorocarbons, J. Amer. Chem. Soc., Vol 70 (September 1948) pp 2994. The present inventors, particularly taking notice of the fact that the above-described substance has a density greater than that of water, has determined the relationship between the average molecular weight and the acoustic impedance to find that the impedance matching between the living body and the substance can easily be attained if the substance has an adequate average molecular weight.

Figure 2:
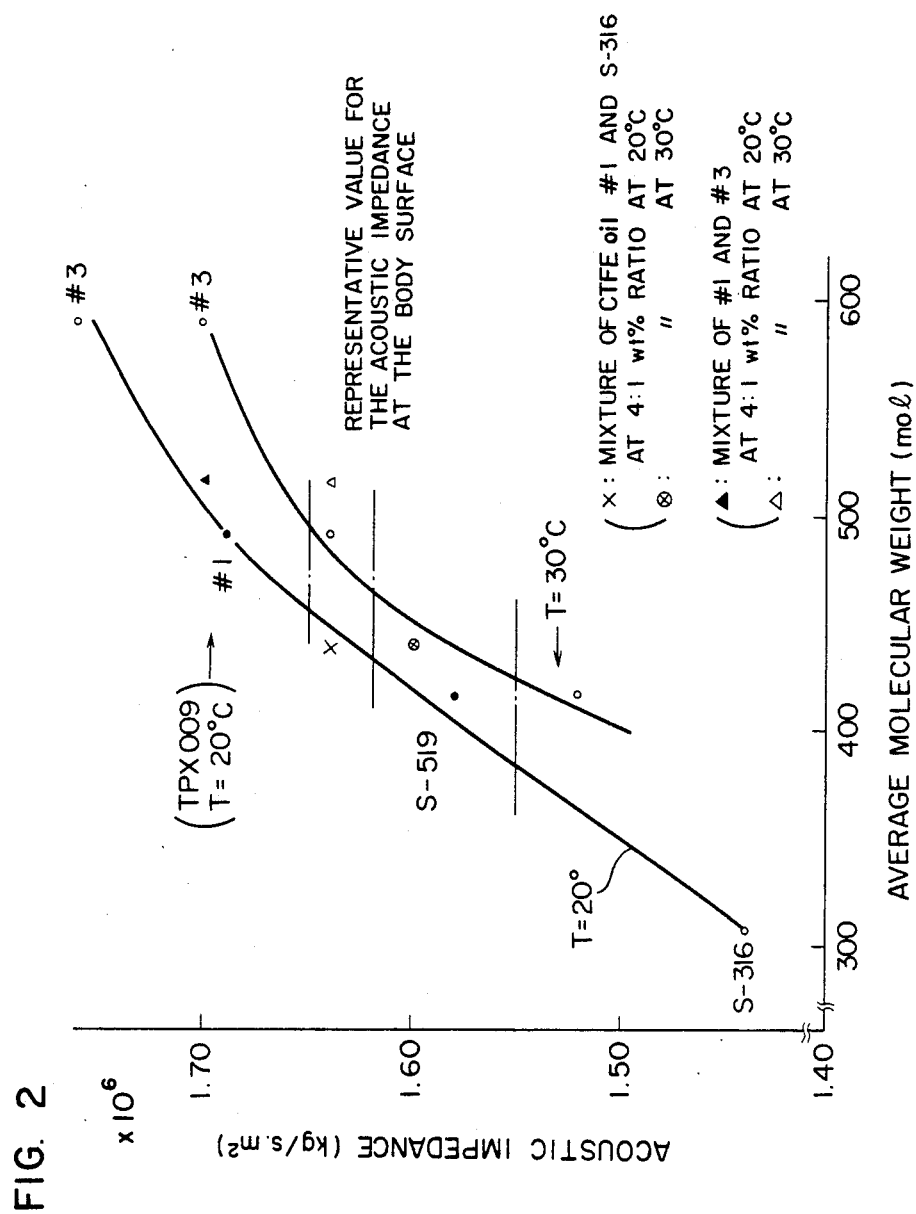

The acoustic impedance of the low molecular weight polymer products from chlorotrifluoroethylene and the mixture thereof shown in FIG. 1 was calculated from the specific gravity measured by a hydrometer in combination with the result of the measurement for the sonic velocity. FIG. 2 shows the relationship between the average molecular weight of the low molecular weight polymer products from chlorotrifluoroethylene shown in Table 1 and the mixture thereof and the acoustic impedance. In the figure, the change of acoustic impedance depending on the temperature is also shown while taking 20° C. and 30° C. as the temperature expected in view of the practical use.

The acoustic impedance at the surface of a human body is considered to reside in the range from $1.55 \times 10^6$ kg/m².sec to $1.65 \times 10^6$ kg/m². sec Reflection echoes from the interface can be reduced by adjusting the acoustic impedance of the above-mentioned low molecular weight polymer products from chlorotrifluoroethylene and the casing for sealing the same with the acoustic impedance at the body surface.

It will be understood from the result of the experiment shown in FIG. 2 that the foregoing purpose can be attained by using the low molecular weight polymer products of chlorotrifluoroethylene with a molecular weight from 400 to 500 or a mixture of them having an average molecular weight in the same range as above.

In the case of using the low molecular weight polymer products from chlorotrifluoroethylene for the probe, they have to satisfy the requirements for the ultrasonic characteristic of velocity and acoustic impedance, as well as electrical insulation property. CTFE oil #1 as the typical example of the low molecular weight polymer products from chlorotrifluoroethylene has an inherent volume resistance at 20° C. of greater than $10^{13}$ ohm-cm, in the liquid of which metal conductor wires or the like can be used with no particular surface insulation. Further, since the fluidizing point is as low as below $-70°$ C. for example, in CTFE oil #1, it is advantageous that the probe having the medium sealed therein would not be damaged due to freezing at low temperature during preservation. Furthermore, it has the excellent properties of neither causing corrosion nor promoting rusting of the metal at all.

Low molecular weight polymer product of chlorotrifluoroethylene also has an effect of swelling or dissolving a certain kind of plastics and rubbers depending on their molecular weight.

Table 3 shows the result of a measurement, in which plastic pieces and cured adhesives are immersed in CTFE oil S-312 and #1, kept therein at 70° C. for one month and, thereafter, taken out, to determine the change in the weight and measure the amount of the substance leached out in the liquid by an infrared spectroscopic analyzer. In the case of soaking them in CTFE oil of a smaller molecular weight of 306.84 and with the following molecular formula:

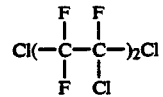

it leaches out the plasticizer in the epoxy resin and increases the volume of the adhesives and the polyurethane to swell them. This leads to an idea that the low molecular weight polymer product of chlorotrifluoroethylene with the molecular weight of greater than 415, that is, a mixture of low molecular weight polymer products of chlorotrifluoroethylene with the molecular formula:

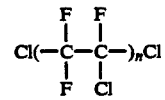

in which n is 3-6 and mixed into a predetermined average molecular weight, little swells of the plastics or leaches out the plasticizer in the plastics and the aging change in the plastics can thus be suppressed. In view of the above, it is considered that the use of the low molecular weight polymer products from the chlorotrifluoroethylene of a smaller molecular weight should be avoided.

In view of the foregoing explanation, it will be understood that use of low molecular weight polymer product of chlorotrifluoroethylene of an adequate molecular weight or a mixture of two or more kinds of low molecular weight polymer products from chlorotrifluoroethylene of different molecular weight can retard the sonic velocity therein as compared with that in the living body and attain the acoustic impedance matching with relation to the living body, as well as provide excellent properties as the acoustic medium of the probe, that is, less corrosive to metals or plastics, non toxic, excellent in electrical insulation property, advantageous in view of the fabrication because of its vapor pressure as low as 0.4 mmHg at 30° C., for example, in CTFE oil #1.

TABLE 3

Test results for immersion of plastics in CTFE oil (S-316 and #1)
(left for one month at 70° C. ambient temperature)

| Number of CTFE oil | Test piece (source and fabrication method) | Initial weight (g) | Weight (g) and change of the weight (%) after one month | Result of infrared spectrum analysis for the CTFE oil after one month |
|---|---|---|---|---|
| #1 Ingredients described in Table 1 | No. 1 Manufactured by EMERSON & CUMING JAPAN K.K. Adhesives: ECOOBOND 45 clear and catalyst 15 clear mixed and cured in 1:1 weight ratio | 2.78 | 2.80 (0.72) | No change |
|  | No. 2 Manufactured by YUKA SHELL EPOXY KABUSIKI KAISHA Epoxy resin: Epicoat 828 and TEPA mixed and cured at 1.6:0.2 weight ratio | 10.38 | 10.38 (0.0) | No change |
|  | No. 3 Manufactured by NIPPON POLYURETHANE INDUSTRY CO. Polyurethane resin: DC-4946 and DC-4954 mixed and cured in 11:9 weight ratio | 2.52 | 2.62 (3.97) | phthalate ester detected slightly |
| S-316 Ingredients described in Table 1 | No. 4 Adhesive (same as No. 1) | 2.62 | 2.74 (4.58) | slight spectral change recognized |
|  | No. 5 Epoxy resin (same as No. 2) | 10.02 | 10.02 (0.0) | remarkable absorption due to phthalate ester |
|  | No. 6 Polyurethane resin (same as No. 3) | 2.22 | 2.46 (10.81) | remarkable absorption due to phtharate ester |

DETAILED DESCRIPTION OF THE PREFERRED EMBODIMENT

Figure 3:
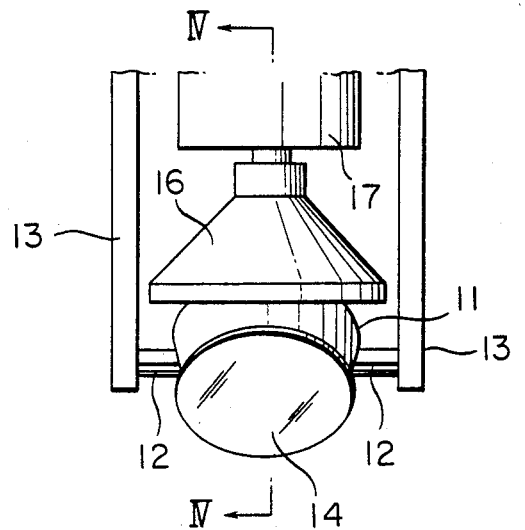
Figure 4:
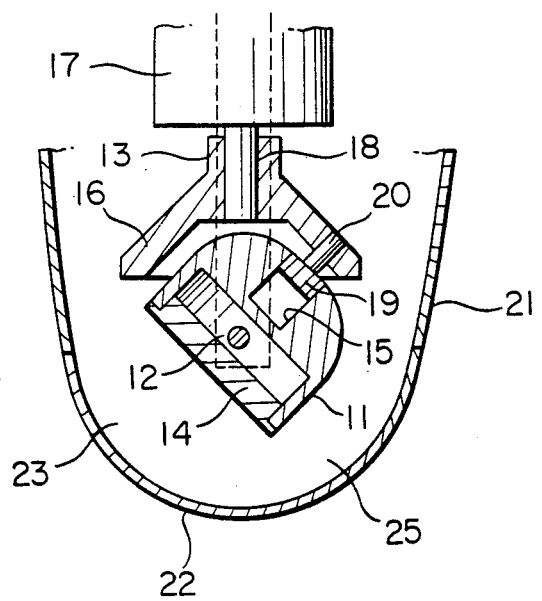
Figure 5:
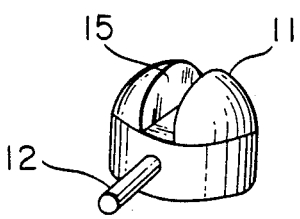

FIGS. 3 through 5 shown the structure of the probe to which the ultrasonic medium according to this invention is applied.

In FIGS. 3 through 5, a support 11 for an oscillator has a cylindrical configuration having a semispherical top. The support 11 is rotatably disposed to a support shaft 12 passing through the cylinder portion thereof. The support shaft 12 is held at both ends thereof to the bearings on arms 13 extended from a support member, so that the support 11 can rotate around the support shaft 12 as the center. A disc-like oscillator 14 is fitted and secured to the recess formed at the lower surface of the support 11, so that it can cause an ultrasonic beam to swing in a sector-like manner within a rotational plane of the support 11 by the reciprocal rotation of the support 11.

As shown in FIG. 4, a driving means for causing the support 11 to rotate reciprocally comprises a linear groove 15 formed in the semi-spherical top so as to make the support 11 in parallel with the center axis of rotation, and a rotor 16 disposed above the support 11. Rotor 16 is formed substantially in a conical shape and attached to a rotating shaft 18 of a motor 17 so that it can rotate around the center axis of the cone. The rotor 16 and the motor 17 are arranged such that the center axis of the rotation of the motor 16 is in perpendicular to the center axis of the rotation of the support 11, and they are fixedly positioned by disposing the motor 17 to the support member as described above. The rotor 16 is attached so that the rotating shaft 18 is at a position apart from the center axis of the rotation of the support 11. Further, a roller 19 is mounted at the inwardly extended end of the rotor 16 by way of a bearing 20 and fitted into the linear groove 15 in the support 11.

In such a driving means, when the rotor 16 is rotated by means of the motor 17, the roller 19 moves along the linear groove 15 under autorotation and, thereby, the support 11 rotates reciprocally around the support shaft 12 as the center. Specifically, when the rotor 16 rotates clockwise, the roller 19 moves along a circle having its center at the center axis of rotation of the rotor 16. Upon such a movement, the roller 19 moves within the linear groove 15 on the support 11 under autorotation and, at the same time, causes the support 11 to rotate counterclockwise around the support shaft 12 as the center. The support 11 rotates to a horizontal status when the rotor 16 rotates by an angle of 90° and rotates in the direction opposite to the above upon further rotation of the rotor 16 by the angle of 90°. Then, when the rotor 16 has rotated along the remaining half circle, the support 11 rotates counterclockwise to return the state shown in the drawing. Accordingly, as the motor 17 continues to rotate the rotor 16, the ultrasonic beam radiated from the oscillator 14 is swung in the sector-like manner by the reciprocal rotation of the support 11.

The support 11, the rotor 16 and the motor 17 are contained in a tightly closed casing 21. The tightly closed casing 21 has window 22 at the positions through which the ultrasonic beam passes for matching the acoustic impedance, and an oil 23 is filled in the inner space 25 of the casing.

The conventional probe uses mineral oil having sonic velocity and acoustic impedance substantially the same as those in the living body as a target to be inspected. In this case, it may be considered that the angle of the ultrasonic beam radiated from the oscillator 14 agrees with the angle of the oscillator 14 swung in the sector-like manner. While on the other hand, the window 22 of the tightly closed casing 21 through which the ultrasonic beam passes is formed with the surface having its center for the curvature positioned at the center of rotation of the oscillator 14, that is, at the center of the support shaft 12 in order to enter the ultrasonic beam with a small area to the body surface of the target to be inspected when the ultrasonic beam is swung in the sector-like manner. The configuration of the entire probe including the tightly closed case 21 can be formed into an elongate shape since the motor 17, the rotor 16 and the support 11 are arranged substantially linearly, the rotor 16 is shaped into a conical shape and the roller 19 is disposed to the inside of the roller 16. In view of the above, the operator can grip the probe easily and firmly to facilitate the inspection.

Figure 6:
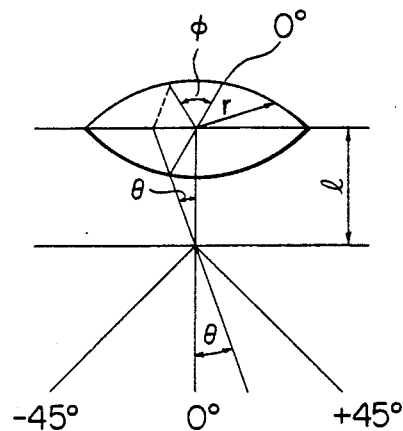

Although the probe of the above-mentioned structure has an advantageous feature that the structure is made simple and small and can be manufactured at a low cost, since the swing angle of the oscillator 14 is not in proportion to the angle of rotation of the motor 17, the interval of the ultrasonic beam can not be deflected in a sector-like manner with an equal angle in the case of radiating ultrasonic pulses at an equal time interval. As shown in FIG. 6, assuming the angle of rotation of the rotor as $\phi$, the swing angle of the oscillator as $\theta$, the radius of rotation of the roller as r, and the distance between the center of rotation of the rotor and the center of rotation of the oscillator as l, the swing angle $\pm 46°$ of the oscillator can be attained by setting the ratio : r/l=1.04.

In the case where the rotor is rotated by the angle $\phi$, the swing angle $\theta$ of the oscillator is given by the following equation.

$$\theta = \tan^{-1}\left(\frac{r \cdot \sin \phi}{l}\right) \quad (1)$$

As described above, if the swing angle of the oscillator is designed as $\pm 46°$, the swing angle $\theta$ is represented as : $\theta = \tan^{-1}(\tan 46 \times \sin \phi)$.

Figure 7:
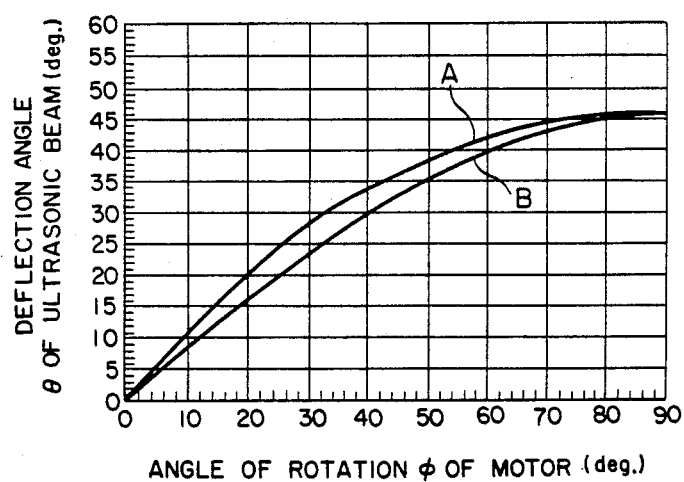

The curve A as shown in FIG. 7 can be obtained for the relationship between the swing angle of rotation $\phi$ of the motor, that is, of the rotor and the swing angle, that is, the deflection angle $\theta$ of the ultrasonic beam by the calculation for the numerical values therebetween. The curve A in this illustrated case is given by setting the ratio as : r/l=1.04.

As can be seen from the example of the calculation shown by the curve A in FIG. 7, the swing angle $\theta$ of the oscillator is not in proportion with the angle of rotation $\phi$ of the rotor. The increment in the swing angle $\theta$ is decreased as the angle of rotation $\phi$ increases.

Figure 8:
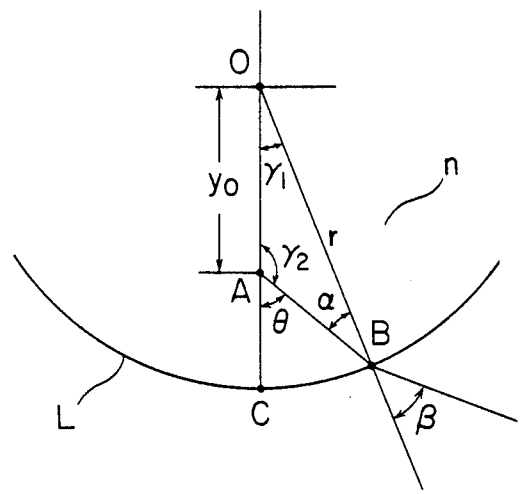

While on the other hand, as shown in FIG. 8 it is considered here such a case wherein an acoustic medium of a refractive index n is sealed within a thin plastic member having a curved plane L and the oscillator is placed in the medium. In this case, it is assumed as below. The curved plane L has a circular cross section and the center for the radius of curvature thereof is situated at O. The radius of the circle is r and the sound source A is positioned at $y_0$ in front of the center O for the circle. The ultrasonic beams radiated from the sound source upon swinging the oscillator propagates in the medium with an angle $\theta$ relative to the extension of the linear segment OA and is then refracted at the intersection B on the interface between the medium and the plastic. Upon this refraction, the angle of incidences and the angle of emittance at the point B relative to the normal line OB are defined as $\alpha$ and $\beta$ respectively.

Since the curved plane L has a cross section equal to the circle with the center at O, the length OB takes a value r. In addition, angle BOA and angle OAB are defined as $\gamma_1$ and $\beta_2$ respectively as illustrated in the figure.

By defining the symbols illustrated in the figure as described above, the following equation can be obtained according to the theory of refraction:

$$n \sin \alpha = \sin \beta \quad (2)$$

In $\triangle$OAB:

$$\gamma_1 + \gamma_2 + \alpha = 180° \quad (3)$$

At the point A on the linear segment OC:

$$\theta + \gamma_2 = 180° \quad (4)$$

The angle of deflection $\theta$ for the ultrasonic beam can be represented as:

$$\theta = \gamma_1 + \beta \quad (5)$$

Equations (3) and (4) are combined as:

$$\gamma_1 + \alpha\theta = 0 \quad (6)$$

According to the equation (2) as described above:

$$\sin \beta = n \sin \alpha \quad (7)$$
$$\beta = \sin^{-1}(n \sin \alpha)$$

Applying the theory of sine to $\triangle$OAB, the equation:

$$\frac{y_0}{\sin \alpha} = \frac{r}{\sin \gamma_2} \quad (8)$$

can be obtained. This equation can be rewritten as:

$$\frac{y_0}{\sin \alpha} = \frac{r}{\sin(180 - \theta)} = \frac{r}{\sin \theta} \quad (9)$$

$$r \sin \alpha = y_0 \sin \theta$$

$$\alpha = \sin^{-1}\left(\frac{y_0 \sin \alpha}{r}\right)$$

It can be understood that $\theta$ can be determined from the foregoing equation if the values are given for n, r, $y_0$, $\theta$.

The following equation can be used conveniently as the equation for calculating the numerical values to determine $\theta$ for given n, r, $y_0$, $\theta$:

$$\alpha = \sin^{-1}\left(\frac{y_0 \sin \theta}{r}\right) \quad \begin{aligned} \gamma_1 &= \theta - \alpha \\ \beta &= \sin^{-1}(n \sin \alpha) \\ \theta &= \gamma_1 + \beta \end{aligned}$$

A relationship between $\phi$ and $\theta$ is shown in FIG. 7 by the curve B, for example, in a case of using low molecular weight polymer product of chlorotrifluoroethylene having a good acoustic impedance matching with the living body as the medium to be sealed within the plastic member, and by determining the relationship between $\theta$ and $\theta$ assuming as : n=1.80, r=60 (mm) and $y_0$=50 (mm) and further determining the relationship between the angle of rotation $\phi$ of the motor and the swing angle $\theta$ of the oscillator.

In this case, r/l in the equation (1) is set to 0.488.

As can be understood from FIG. 7, low molecular weight polymer product of chlorotrifluoroethylene, for example a mixture of CTFE oil #1 and CTFE oil S-316 in 4:1 weight ratio is sealed into the probe of the structure shown in FIGS. 3 through 5, as the liquid medium in which the sonic velocity is lower and which has the acoustic impedance nearly to that of the living body.

As compared with the conventional probe using the liquid medium having the sonic velocity and acoustic impedance similar to those of the living body, the deflection angle $\theta$ of the ultrasonic beam relative to the angle of rotation $\phi$ of the motor is more proportional and the frame rate can be improved according to this invention.

Figure 9:
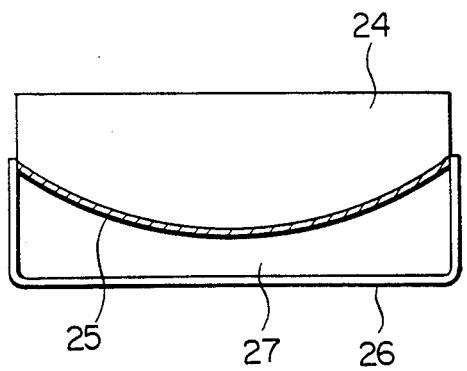

FIG. 9 shows an embodiment in which the deflection angle of the ultrasonic beam is increased by utilizing the fact that the sonic velocity is lower in low molecular weitht polymer product of chlorotrifluoroethylene and applying this to a probe comprising oscillator elements each with a narrow width arranged in a curved surface. In this embodiment, a sound absorbing material 24, oscillator elements 25 arranged in a curved plane, a casing 26 made of plastics having an acoustic impedance nearly equal to that of the living body and low molecular weight polymer product of chlorotrifluoroethylene 27 are the same as those used in the mechanical scanning probe as described above.

As shown in the figure, the liquid medium constitutes a concaved lens combined with a probe arranged in a convexed manner such that the surface in contact with the living body forms a flat plane and the deflection angle of the ultrasonic beam is enlarged based on the same principle in the mechanical scanning probe as described already.

As described above, the following advantageous effects can be obtained according to this invention.

(1) It is possible to optionally design the probe such that the sonic velocity through the liquid medium is significantly lower (less than 900 m/sec) than that in the living body and the acoustic impedance thereof can be adjusted nearer to the value of that of the living body.

(2) It can satisfy the acoustic physical property, as well as electrical properties, viscosity and safety factor which are important as the practical apparatus and, in addition, the liquid medium is less evaporative.

What is claimed is:

1. An ultrasonic probe comprising osillator means and an acoustic medium, said acoustic medium adapted to be in contact with said oscillator means, in which at least one low molecular weight polymer product from chlorotrifluoroethylene is used as the acoustic medium.

2. An ultrasonic probe as defined in claim 1, wherein a mixture of a plurality of low molecular weight polymer products of chlorotrifluoroethylene having an average molecular weight of from 400 to 500 is used as the acoustic medium.

3. An ultrasonic probe as defined in claim 2, wherein a mixture of low molecular weight polymer products from chlorotrifluoroethylene represented by the general formula:

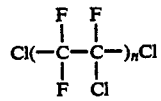

where n is an integer from 1 to 6 is used as the acoustic medium.

4. An ultrasonic probe as defined in claim 3 where n is an integer from 3 to 6.

5. An ultrasonic probe as defined in claim 1, wherein said at least one polymer product from chlorotrifluoroethylene is represented by the formula:

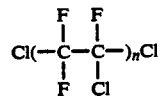

where n is an integer from 1 to 6.

6. An ultrasonic probe as defined in claim 5, wherein n is an integer from 3 to 6.

7. An ultrasonic probe as defined in claim 1, adapted to be used in diagnosis of a living body, wherein the acoustic medium has an acoustic impedance matching that of the living body, and the sonic velocity in the acoustic medium is less that that in the living body.

8. An ultrasonic probe as defined in claim 7, wherein a mixture of a plurality of the low molecular weight polymer products are used as the acoustic medium, the low molecular weight polymer products of the mixture being selected so as to provide a mixture having an acoustic impedance matching that of the living body.

9. An ultrasonic probe comprising,
means for radiating an ultrasonic beam;
a casing; and
a liquid acoustic medium in contact with said means for radiating said ultrasonic beam and contained in said casing; wherein said liquid acoustic medium comprises at least one low molecular weight polymer product from chlorotrifluoroethylene.

10. An ultrasonic probe as defined in claim 9, wherein said liquid acoustic medium has a molecular weight in the range of 400–500.

11. An ultrasonic probe as defined in claim 9, wherein said liquid acoustic medium consists essentially of a mixture of two or more low molecular weight polymer products from chlorotrifluoroethylene having different molecular weights and wherein said acoustic has an average molecular weight in the range of 400–500.

12. An ultrasonic probe as defined in claim 9, wherein said at least one low molecular weight polymer product from chlorotrifluoroethylene is represented by the formula:

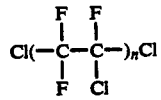

where n is an integer from 1 to 6.

13. An ultrasonic probe as defined in claim 12, wherein n is an integer form 3 to 6.

14. An ultrasonic probe as defined in claim 9, wherein said liquid acoustic medium consists essentially of a mixture of low molecular weight polymer products from chlorotrifluoroethylene represented by the formula:

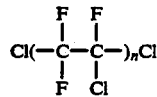
where n is an integer from 1 to 6 and whereing said liquid acoustic medium has an average molecular weight in the range of 400–500.
15. An ultrasonic probe as defined in claim 14, wherein n is an integer 3 to 6.
16. An ultrasonic probe as defined in claim 9, wherein said means for radiating said ultrasonic beam includes means for oscillating said ultrasonic beam.
* * * * *